United States Patent [19]

Inouye et al.

[11] Patent Number: 5,139,937
[45] Date of Patent: Aug. 18, 1992

[54] PROCESS FOR PRODUCING APOAEQUORIN

[75] Inventors: Satoshi Inouye, Yokohama; Shigeyuki Aoyama, Ichihara; Yoshiyuki Sakaki, Fukuoka, all of Japan

[73] Assignee: Chisso Corporation, Osaka, Japan

[21] Appl. No.: 272,900

[22] Filed: Nov. 18, 1988

[30] Foreign Application Priority Data

Nov. 18, 1987 [JP] Japan .................. 62-291640

[51] Int. Cl.⁵ ............... C07K 3/22; C07K 3/24; C07K 15/08; C12P 21/00
[52] U.S. Cl. ................... 435/69.1; 530/350; 530/416; 530/419; 530/420
[58] Field of Search .......... 530/350, 855, 808, 809, 530/825, 416, 417, 419, 420, 427; 435/69.1

[56] References Cited

U.S. PATENT DOCUMENTS 4,643,969 2/1987 Inouye et al. .............. 435/172.3

FOREIGN PATENT DOCUMENTS 226979 7/1987 European Pat. Off. .......... 435/69.1
264819 4/1988 European Pat. Off. .......... 435/69.1
61-135586 6/1986 Japan .
61-249098 10/1986 Japan .

OTHER PUBLICATIONS

Ghrayeb et al., "Secretion cloning vectors in Escherichia coli", EMBO Journal 3:2437-42 1984.
Prasher et al., "Cloning and Expression of the cDNA Coding for Aequorin . . . ", Biochem. Biophys. Res. Comm. 126:1259-68, 1985.
Tsuji et al., "Site-specific mutagenesis of the calcium-binding photoprotein aequorin," PNAS 83:8107-11, Nov. 1986.
Bjurstrom, "Biotechnology", Chemical Engineering Feb. 18, 1985, pp. 126, 142-143, 151-154.
Inouye et al., "Cloning and sequence analysis of cDNA for the luminescent protein aequorin," PNAS vol. 82, pp. 3154-3158, May 1985.
Johnson et al., "Introduction to the Bioluminescence of Medusae . . . ", Methods in Enzymology LVII, 1978, pp. 271, 287-290.
Prasher et al., "Isolation and Expression of a cDNA Coding for Aequorin . . . ", Methods in Enzymology vol. 133, 1986, pp. 288-298.

Primary Examiner—Jeffrey E. Russel
Attorney, Agent, or Firm—Wenderoth, Lind & Ponack

[57] ABSTRACT

A process for producing the protein part of $Ca^{+2}$-binding photoprotein aequorin (apoaequorin) according to a recombinant DNA technique, and a process for purifying the resulting apoaequorin are provided, which production process comprises cultivating a strain having an expression vector piP-HE outside the bacterial bodies transformed into Escherichia coli, followed by separating the resulting culture solution into the bacterial bodies and a culture filtrate, and recovering the culture filtrate, and which purification process comprises adding an acid to the culture filtrate so as to give a pH of 4.7 or less, followed by recovering the resulting white precipitates, dissolving the white precipitates in a buffer solution, reducing the solution, subjecting the resulting apoaequorin fraction to adsorption treatment according to anion exchange chromatography and subjecting the resulting apoaequorin to gel filtration.

4 Claims, 4 Drawing Sheets

PROCESS FOR PRODUCING APOAEQUORIN

BACKGROUND OF THE INVENTION

1. Field of the Invention

This invention relates to a process for producing the protein part of Ca-binding photoprotein aequorin (i.e. apoaequorin) employing a recombinant DNA technique, characterized by recovering the apoaequorin outside the bacterial cells and a process for purifying the apoaequorin from the filtrate of the resulting culture media.

2. Description of the Related Art

Natural aequorin is a photoprotein present in the cells existing on the periphery of the umbrella of photogenic Aequorea growing near the Harber island, Friday, Wash., U.S.A., and only about 200 mg of purified aequorin is obtained from about 5 tons of Aequorea.

Since this photoprotein aequorin is specifically bound with $Ca^{++}$ ion to emit light, it has been utilized for various analyses. However, since the quantity fed is insufficient, its availability (in the analysis utilizing a faint light emittance) has not yet been sufficiently effected.

Recently, the present inventors have succeeded in producing a recombinant aequorin having an aequorin activity, by producing the protein part of aequorin (apoaequorin) according to recombinant DNA technique, followed by mixing it with a reducing agent, a substrate, etc. (Japanese patent application Nos. Sho 60-280259/1985 and Sho 61-249098/1986).

However, production of apoaequorin in a large quantity and its purification have not yet been achieved. Thus, we have investigated various culture conditions using an expression vector piP-HE outside the bacterial bodies (Japanese patent application No. Sho 61-249098/1986). As a result, it has become possible to detect production of apoaequorin outside the bacterial cells i.e. in the culture filtrate in a similar quantity (20 μg-50 μg/ml) to that in the bacterial cells.

SUMMARY OF THE INVENTION

As apparent from the foregoing, the object of the present invention is to provide a process for producing apoaequorin outside the bacterial cells and a process for purifying the same.

The present invention in two aspects has the following main constitutions (1) and (2) and constitutions as embodiments thereof (3), (4) and (5):

(1) a process for producing apoaequorin which comprises cultivating a strain of *Escherichia coli* transformed with an expression vector piP-HE, followed by separating the resulting culture solution into the bacterial cells and a culture filtrate and recovering the culture filtrate;

(2) a process for producing apoaequorin which comprises cultivating a strain of *Escherichia coli* transformed with an expression vector piP-HE, followed by separating the resulting culture solution into the bacterial bodies and a culture filtrate, adding an acid to the culture filtrate so as to give a pH of 4.7 or less and recovering the resulting white precipitates;

(3) a process according to item (2), which comprises further dissolving said white precipitates in a buffer solution, followed by subjecting the resulting solution to reduction treatment with a reducing agent;

(4) a process according to item (3), which comprises further subjecting apoaequorin fraction subjected to the reduction treatment, to adsorption treatment according to anion exchange chromatography; and (5) a process according to item (3), which comprises further subjecting apoaequorin fraction subjected to the reduction treatment, to adsorption treatment according to anion exhange chromatography and further subjecting the resulting apoaequorin to gel filtration treatment.

BRIEF DESCRIPTION OF THE DRAWINGS

FIG. 1 shows a view illustrating construction of expression secretory vector piP-HE used in the present invention.

FIG. 2 shows a view illustrating confirmation of production of apoaequorin by means of *Escherichia coli* having piP-HE.

FIG. 3 shows a chart illustrating a relationship between the culture time of *Escherichia coli* having piP-HE and the production of apoaequorin.

FIG. 4 shows a chart illustrating the results of chromatography of apoaequorin by means of DEAE-porous cellulose spherical particles.

FIG. 5 shows a view illustrating the confirmation results of apoaequorin purity by means of SDS-polyacrylamide gel electrophoresis.

DETAILED DESCRIPTION OF PREFERRED EMBODIMENTS

The constitutions and effectiveness of the present invention in two aspects will be described in more detail.

The strain used in the present invention refers to a strain of *Escherichia coli* transformed an expression vector. This piP-HE has been described in detail in Japanese patent application No. Sho 61-249098/1986 the invention of which has been made by the present inventors and a view of piP-HE construction steps illustrating its constitution is shown in FIG. 1 of the accompanying drawings.

Figure 1:
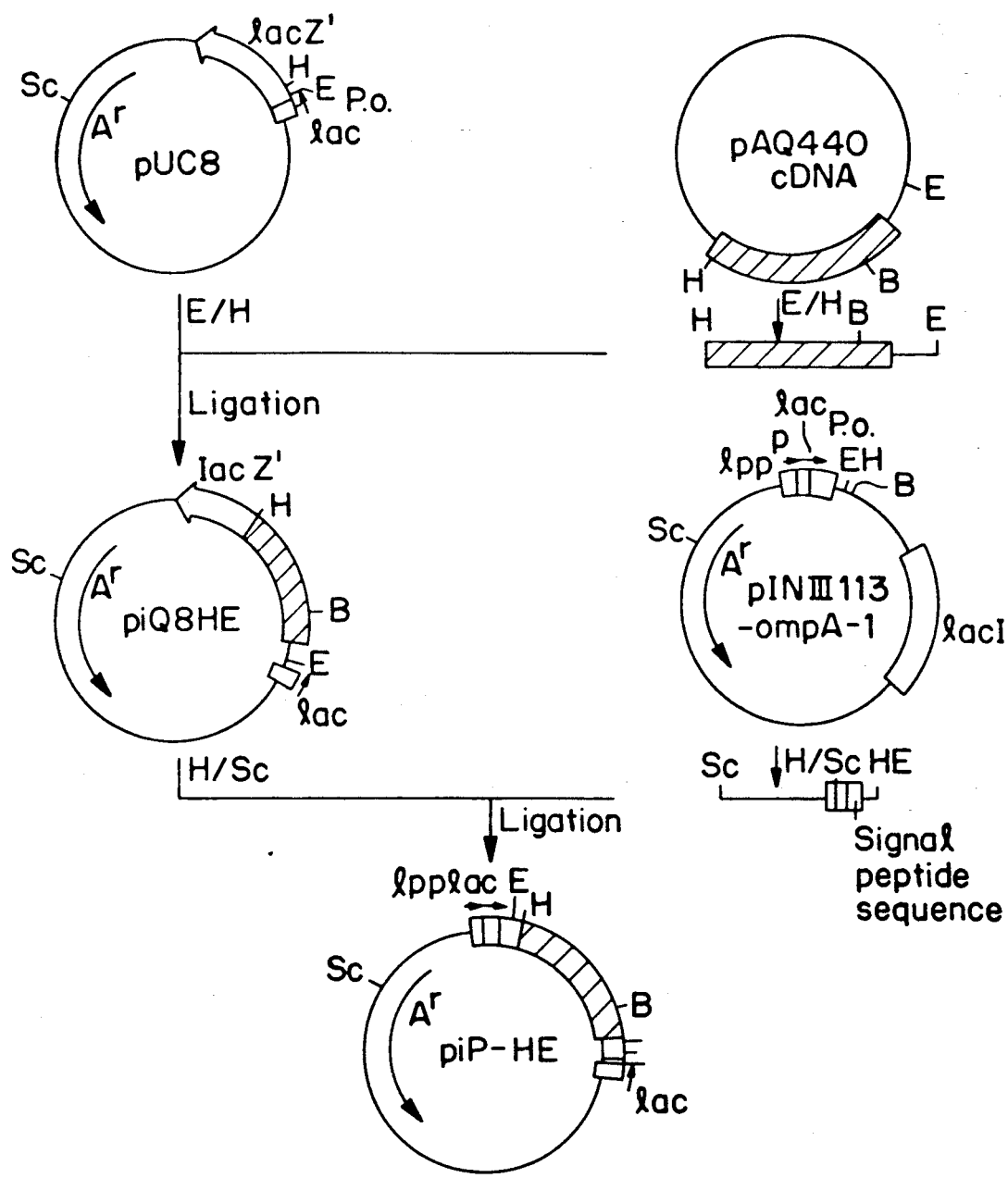
FIGS. 1-5 each show a view illustrating an embodiment of the present invention.

In FIG. 1, pUC8 is a high copy cloning vector and pAQ440 is a clone plasmid of photoprotein aequorin. piQ8HE is prepared from the above two as shown in the figure, followed by inserting into the Sca I/Hind III part of the above piQ8-HE, a fragment cut off from pIN III 113 ompA-1 and containing a promoter of lipoprotein (lpp.P), a promotor and an operator of lactose operon(lacPO) and a signal peptide region to construct piP-HE.

Transformation of piP-HE into *Escherichia coli* may be carried out according to a known method. Examples of preferred *Escherichia coli* are D1210 and LE392.

A. Culture conditions of *Escherichia coli*

(Production conditions)

*Escherichia coli* having piP-HE is cultivated in a suitable medium such as L-medium. Its culture conditions have no particular limitation, but for example, shaking culture is carried out at 37° C. overnight. It is preferred to add a suitable quantity (e.g. 50 μg/ml) of Ampicillin to the medium.

A portion of the thus obtained culture solution is added to M9 medium (see Example mentioned later as to its composition example) in a quantity of about 100 times the quantity of the above portion, followed by shaking culture. It is preferred to add a small quantity of 0.2% Casamino acid (trademark of product made by Difco Company) to the medium.

The culture temperature is 30° to 42° C., preferably 40° C. and the culture time is about 12 to 20 hours.

Figure 2:
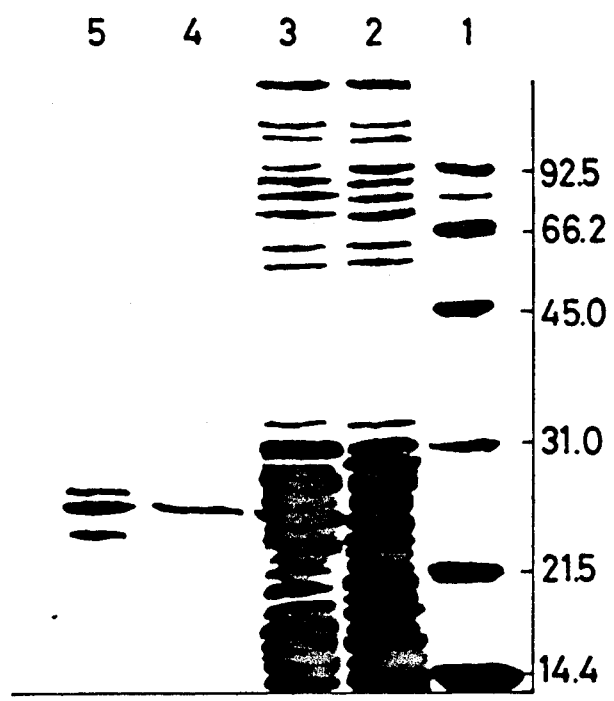

By way of the above-mentioned culture, a large quantity of apoaequorin is produced at the part outside of the bacterial cells in the culture solution. Confirmation of the thus produced apoaequorin is possible according to SDS-polyacrylamide gel electrophoresis on the basis of molecular weight marker and natural aequorine, as shown in FIG. 2 relative to Example mentioned later. In this figure, numerals 1-5 have the following meanings, respectively:

1: molecular weight marker
2: cells of *Escherichia coli* containing pUC8 (corresponding to 200 μl)
3: cells of *Escherichia coli* containing piP-HE (ditto)
4: culture filtrate of *Escherichia coli* containing piP-HE (corresponding to 50 μl)
5: natural aequorin (5 μg)

FIG. 2 evidently shows that a large quantity of apoaequorin has been detected outside the bacterial cells.

Figure 3:
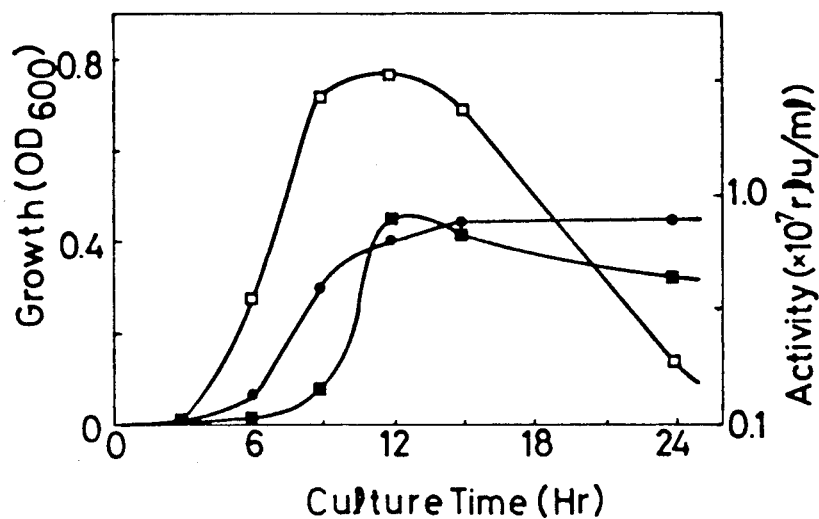

FIG. 3 relative to Example mentioned later shows the results of confirmation of apoaequorin production carried out with the above-mentioned culture substance by means of 12.5% by weight of SDS-polyacrylamide gel.

In this figure,

—●— shows production of *Escherichia coli* (D1210) having piP-HE.
—□— shows aequorin activity in the bacterial cells.
—■— shows aequorin activity of the culture filtrate.

As apparent from the figure, a sufficient quantity of apoaequorin has been produced in the resulting purified substance B. Separation process of bacterial bodies The culture solution obtained in the above item A is separated into bacterial cells and culture filtrate according to the known method. The separation process has no particular limitation, but the bacterial cells are separated by subjecting the solution to centrifugal treatment preferably for about 5 to 15 minutes preferably by means of a high-speed centrifuge to obtain a culture filtrate. The treating temperature may be in the range of 0° C. to the culture temperature, and the treatment may be carried out usually at room temperature (15° to 25° C.) without any obstacle. The aequorin activity of the resulting culture filtrate is as described above in item A.

C. Concentration of apoaequorin from culture filtrate

When the culture filtrate obtained above in item B is subjected to acidic treatment as described below, concentrated apoaequorin is obtained. The acidic treatment refers to a treatment of adding an acid to the culture filtrate to make its pH about 5 or lower, preferably 4.7 or lower. The kind of the acid has no particular limitation, but it is preferably weak acids, particularly water-soluble organic acids. Its concrete examples are inorganic acids such as dilute hydrochloric acid, dilute sulfuric acid, etc., aliphatic monocarboxylic acids such as trichloroacetic acid, formic acid, acetic acid, propionic acid, butyric acid, etc., aliphatic polycarboxylic acids such as oxalic acid, maleic acid, etc., aromatic carboxylic acids such as benzoic acid, cinnamic acid, etc., and aliphatic oxycarboxylic acids such as ascorbic acid, citric acid, etc.

The mixing manner of such acids with the culture filtrate has no particular limitation, but it is preferred to dropwise add an acid or its aqueous solution to the culture filtrate under agitation to gradually lower the pH of the filtrate (note: the pH prior to the acid addition is generally about 6.8-7.2). The above acid treatment is carried out at 0° to 40° C., preferably 0° to 15° C., for 5 minutes to 2 hours, followed by allowing the resulting material to stand at 0° to 4 ° C. for 1 to 30 hours, preferably 5 to 15 hours.

Apoaequorin is deposited in the form of white precipitates during the treatment of the pH reduction, and by allowing the resulting filtrate to stand after the acid treatment, precipitation is completed to improve the yield. The thus obtained precipitates (concentrated apoaequorin) is separated from the culture filtrate. The separation manner has no particular limitation, but usually, centrifugal separation method is employed.

D. Treatment with reducing agent

The concentrated apoaequorin obtained above in item C is dissolved in a suitable buffer (such as those containing 100 mM Tris-HCl (pH 7.6) and 10 mM EDTA), followed by adding a definite reducing agent to the solution. An example of such reducing agent is 2-mercaptoethanol, but other reducing agents which are similarly usable may, of course, be used.

As to the reduction conditions, a reducing agent is added to and mixed with the concentrated apoaequorin so as to give a concentration of the reducing agent in the concentrated apoaequorin solution, of 1 to 30 mM, preferably 5 to 15 mM, followed by allowing the mixture to stand at 0° to 15° C., preferably 0° to 5° C. for 1 to 10 hours, preferably 2 to 6 hours to advance the reduction. Thus, an apoaequorin fraction subjected to reduction treatment is obtained.

By such a treatment with a reducing agent, the —S—S— bond formed in apoaequorin is dissociated into —SH HS—. By carrying out the treatment with a reducing agent, the apoaequorin yield (percentage recovery) by way of anion exchange chromatography is improved by 30% or more. Further, the separation is improved.

E. Anion exchange chromatography

The object of this step is to concentrate and purify apoaequorin. The reduction-treated apoaequorin obtained above in item D is adsorbed onto an anion exchange resin. Concrete chromatography has no particular limitation, but it is preferred to employ a column chromatography with DEAE-porous cellulose spherical particles (Cellulofine (trademark of product made by Chisso Corporation)).

The column employed is in advance neutralized with a buffer (e.g. 30 mM Tris-HCl buffer, pH 7.6) containing definite quantities of EDTA and 2 mercaptoethanol.

The apoaequorin subjected to reduction treatment with a reducing agent is adsorbed onto the column, followed by washing with the above-mentioned buffer solution, and when the absorbance of the washing solution reached a definite value (0.01 (280 nm)), carrying out the subsequent elution and fractionation.

Figure 4:
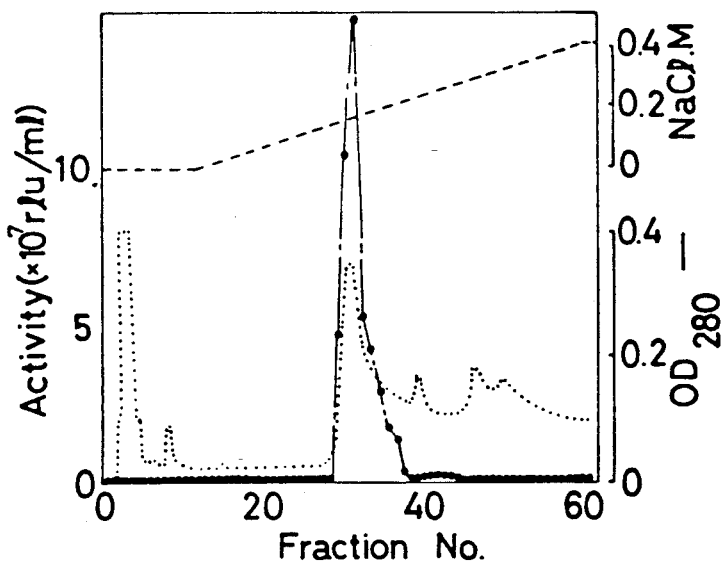

Namely, the eluation of apoaequorin is carried out at a NaCl linear concentration gradient of 0→0.4M, and fractionation is carried out in a definite quantity (e.g. each 8 ml). The eluation flow rate has no particular limitation, but it is e.g. 10 to 40 ml/hr., preferably 20 to 30 ml/hr. FIG. 4 relative to Example mentioned later shows the results of the above-mentioned column chromatography.

In this figure, the respective curves have the following meanings:

—●—: aequorin activity
- - - -: NaCl salt concentration gradient
••••: absorbance at $OD_{280}$ In view of the figure, aequorin activity was detected in an eluate at a part having a salt concentration of 0.15 to 0.2M.

Figure 5:
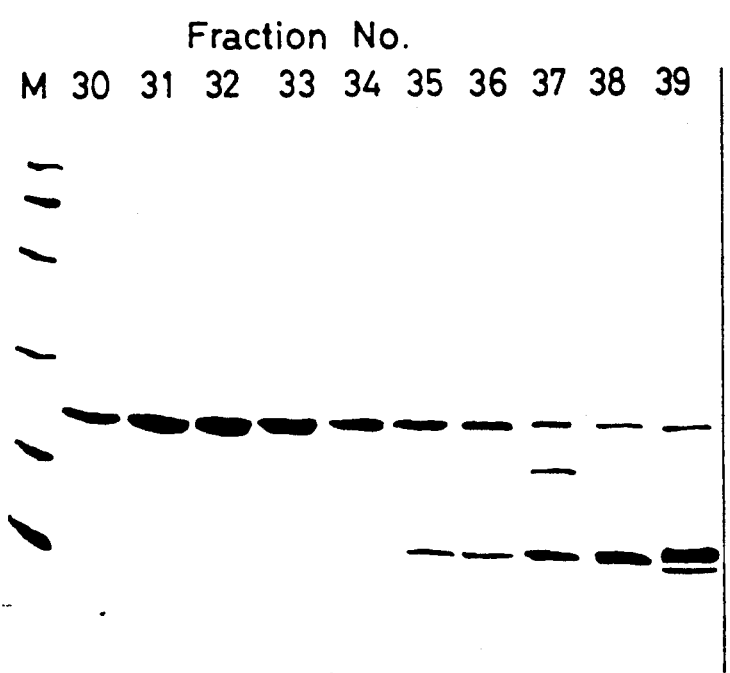

FIG. 5 relative to Example mentioned later shows the results obtained by checking the apoaequorin purity at the above part according to 12.5% by weight SDS-polyacrylamide gel electrophoresis.

In this figure, M shows a molecular weight marker. The apoaequorin purities of the respective fractions were measured by means of a densitometer (Dual-wavelength chromato scanner CS-93 (tradename of instrument manufactured by Shimazu Seisakusho Co., Ltd.)). In Example mentioned later, a fraction having the maximum concentration had a purity of 95% or higher.

F. Gel filtration

As to the apoaequorin obtained above in item E, when a higher purity is required, the instant step is carried out.

For example, a column of Sephadex G-100 (trademark of product made by Pharmacia Co., Ltd.) (1.8×100 cm) is leveled with a 30 mM Tris-HCl (pH 7.6) containing 10 mM EDTA and 1 mM mercaptoethanol, followed by feeding apoaequorin eluted by DEAE-ion chromatography described above in item E, to the column and treating it. The flowing out rate has no particular limitation, but it is in the range of 2 to 10 ml/hr., preferably 5 ml/hr.

The process of the present invention described above is very effective and important in the protein purification. By using a synthetic medium for the culture solution, it is also possible to prevent impurities from mixing therein, and by allowing apoaequorin to effect secretory production in the culture filtrate, the subsequent purification becomes easy. Namely, apoaequorin occupies 60% by weight or more of the protein in the culture filtrate, and by utilizing acidic treatment as an easy concentration process, concentration from the culture filtrate has become possible.

Further, according to the reduction treatment with a reducing agent such as 2-mercaptoethanol, followed by chromatography with an anion exchange material (DEAE-Cellulofine), apoaequorin having a purity of 95% or higher (about 7 mg) was obtained from 200 ml of the culture filtrate. This yield corresponds to the quantity of apoaequorin separated from about 150 Kg of Aequorea.

Due to establishment of production conditions of apoaequorin by way of a secretory vector outside the bacterial cells as well as establishment of its purification process, aequorin production in a large quantity has become possible and effectiveness brought about therefrom is great.

The present invention will be described in more detail by way of Example.

EXAMPLE

A strain having an expression vector outside the bacterial bodies (piP-HE) transformed in *Escherichia coli* is used. Examples of preferred *Escherichia colis* are D1210, LE392, etc. The plasmid of the piP-HE is shown in FIG. 1.

A process for producing apoaequorin expressed with the above-mentioned strain and its purification process will be described below.

(1) Culture conditions of *Escherichia coli* (production conditions)

*Escherichia coli* having piP-HE was subjected to shaking culture in a suitable medium containing Ampicillin (50 μg/ml) (e.g. L-medium: Bactotryptone 10 g, yeast extract 5 g and NaCl 5 g in 1 l) (10 ml) at 37° C. overnight.

The resulting culture solution (2 ml) was added to M9 medium containing 0.2% Casamino acid ($Na_2HPO_4$ 6 g, $KH_2PO_4$ 3g, NaCl 0.5 g, $NH_4Cl$ 1 g, 0.2% glucose, 2 mM $MgCl_2$ and 0.1 mM $CaCl_2$ in 1 l), followed by shaking culture at 37° C. for 20 hours.

FIG. 2 shows the relationship between apoaequorin formed inside and outside the bacterial bodies and its growth outside the bacterial cells. As apparent from this figure, a large quantity of apoaequorin was detected outside the bacterial cells. FIG. 3 shows that formation of apoaequorin was confirmed with 12.5% SDS-polyacrylamide gel.

It was found that 20 to 50 μg/ml of apoaequorin was formed in the culture filtrate, and such a quantity was sufficient for purifying apoaequorin.

(2) Process for separating bacterial cells

Separation of the bacterial cells and the culture filtrate from the culture solution was carried out. Namely, the bacterial cells were separated according to centrifugal separation by means of a high-speed centrifuge (6,000×g, 10 min.).

(3) Process for concentrating apoaequorin from the culture filtrate

The culture filtrate separated from the bacterial cells was subjected to an acidic treatment. The acidic treatment refers to making the pH of the culture filtrate 4.7 or less. In order to lower the pH, the pH was made 4.2 with 1N acetic acid with stirring. As the pH lowered, white precipitates of apoaequorin appeared, and when the filtrate was allowed to stand overnight at 4° C., a good percentage recovery was obtained.

The above white precipitates obtained by allowing it to stand overnight were separated by means of centrifugal separation (9,000×g/10 minutes). The thus obtained precipitates are concentrated apoaequorin.

(4) Treatment with reducing agent

The above concentrated apoaequorin was dissolved in a buffer containing 100 mM Tris-HCl (pH 7.6) and 10 mM EDTA, followed by adding a reducing agent. 2-Mercaptoethanol as a preferred reducing agent was added so as to give a final concentration of 10 mM, followed by allowing the mixture to stand at 4° C. for 2 hours or longer.

(5) Anion exchange chromatography

Apoaequorin fraction subjected to treatment with the reducing agent was adsorbed according to anion exchange chromatography. In this case, a DEAE-Cellulofine (trademark of porous cellulose spherical particles) A800 (1.0×10 cm) column chromatography was employed.

The column employed was in advance leveled with a 30 mM Tris-HCl (pH 7.6) buffer containing 10 mM EDTA and 1 mM 2-mercaptoethanol, followed by allowing the apoaequorin treated with the reducing agent to adsorb onto the column, then washing it with the same buffer, confirming that the absorbance reached 0.01 (280 nm) or less, thereafter dissolving out apoaequorin at a linear concentration gradient of 0→0.4 M NaCl and fractionating the respective apoaequorin fractions each in 8 ml. The dissolving-out flow rate was 24 ml/hr.

FIG. 4 shows the results of the chromatography. Aquorin activity was detected at a salt concentration of 0.15 to 0.2M. This shows that apoaequorin is present at this part. Its purity was detected with 12.5% SDS-polyacrylamide gel. FIG. 5 shows the results. The purity obtained with fractions 30 to 33 by means of a densitometer (Dual-wavelength chromatoscanner CS-930 (trademark of instrument made by Shimazu Seisakusho Company)) was 95% or higher.

The respective yields at the purification steps (1) to (5) are collectively shown in Table 1. Apoaequorin having a purity of 95% or higher was obtained in about 7 mg.

TABLE 1

Summary of apoaequorin purification

| Step | Total protein (mg) | Total activity ($\times 10^9$ rlu) | Yield (%) | Specific activity ($\times 10^9$ rlu/mg) | Total volume (ml) |
| --- | --- | --- | --- | --- | --- |
| 1 Culture solution | 47.6 | 10.7 | 100 | 0.224 | 200 |
| 2 Acid-treated product | 24.3 | 6.78 | 63 | 0.279 | 8.5 |
| 3 *1-treated product | 7.4 | 2.84 | 27 | 0.383 | 24 |

(Note)
*1: DEAE Cellulofine-A800

However, 1 μg of natural aequorin corresponds to $4 \times 10^5$ r lμ (relative photogenic value).

What we claim is:

1. A process for producing apoaequorin which comprises cultivating a strain of *Escherichia coli* transformed with an expression vector piP-HE in a culture medium and filtering the culture medium to recover a filtrate containing apoaequorin and wherein the filtrate is acidified to a pH of 4.7 or less to produce a white precipitate and recovering said white precipitate which contains apoaequorin.

2. The process according to claim 1, which comprises further dissolving said white precipitates in a buffer solution, followed by subjecting the resulting solution to reduction treatment with a reducing agent.

3. The process according to claim 2, which comprises further subjecting said white precipitate subjected to the reduction treatment, to adsorption treatment by anion exchange chromatography.

4. The process according to claim 3, which comprises further subjecting said white precipitate subjected to the reduction treatment, to adsorption treatment by anion exchange chromatography and further subjecting the resulting apoaequorin to gel filtration treatment.

* * * * *